United States Patent [19]
Bouck et al.

[11] Patent Number: 5,192,744
[45] Date of Patent: Mar. 9, 1993

[54] METHOD OF INHIBITING ANGIOGENESIS OF TUMORS

[75] Inventors: Noel P. Bouck, Oak Park; Peter J. Polverini, Evanston; Deborah J. Good, Chicago, all of Ill.; Farzan Rastinejad, Los Altos, Calif.

[73] Assignee: Northwestern University, Evanston, Ill.

[21] Appl. No.: 464,369

[22] Filed: Jan. 12, 1990

[51] Int. Cl.$^5$ .................... A61K 37/02; C07K 15/06; C07K 15/14
[52] U.S. Cl. .................................. 514/8; 514/12; 514/21; 530/380; 530/381; 530/395
[58] Field of Search ............... 530/380, 381, 395, 829; 514/8, 12, 21

[56] References Cited

U.S. PATENT DOCUMENTS

| | | | |
|---|---|---|---|
| 4,182,753 | 1/1980 | Saltarelli | 530/395 |
| 4,820,505 | 4/1989 | Ginsberg et al. | 530/387 |
| 4,883,755 | 11/1989 | Carabasi et al. | 435/240.2 |
| 4,898,732 | 2/1990 | Fernandez | 424/422 |
| 5,001,116 | 3/1991 | Folkman et al. | 514/56 |

OTHER PUBLICATIONS

Chemical Abstract 111:75630z (1989).
Biosys Abstract 82036810 (1986).
Rastinejad, "Regulation of the Activity of a New Inhibitor of Angiogenesis by a Cancer Suppressor Gene". *Disertation Abstracts International.* vol. 49, No. 11, May 1989, p. 4678-B.
Creighton, *Proteins.* W. H. Freeman and Co. 1984. pp. 76-77.
Rastinejad et al., Proceedings, 79th Meeting, Amer. Assoc. Cancer Res., 29:455, Abstract 1809 (Mar., 1988).
Bouck et al., In vitro Cell and Devel. Biol. 21:463 (1985).
Good et al., UCLA Symposia, Jan. 21-Feb. 11, 1989, J. Cellular Biochem., Suppl. 13B:30, Abstract D215.
Bouck et al., Current Commun. Molecular Biol. in "Recessive Oncogenes and Tumor Suppression", Cavenee et al., eds. pp. 179-183 (Cold Spring Harbor Laboratory Press, 1989).
Rastinejad et al., Cell, 56:345-355 (Feb. 10, 1989).
Santoro and Frazier, Methods in Enzymology, 144:438-446 (1987).
Majack and Bornstein, Cell Membranes Methods-Reviews, 3:55-77 (1987).
Haverstick et al, Biochemistry, 23:5597-5603 (1984).
Lawler and Hynes, J. Cell. Biol., 103:1635-1648 (1986).
Donoviel, J. Biolg. Chem., 263:18590-18593 (1988).
Hennessy et al., J. Cell. Biol., 108:729-736 (1989).
Bouck et al., Cancer Res., 46:51-1-5105 (1986).
Rastinejad et al., Proceedings, 78th Ann. Meeting, Amer. Assoc. Cancer Res., vol. 228:61, Abstract 241 (Mar., 1987).
Bouck et al, UCLA Symposia, Feb. 3-Mar. 11, 1990, J. Cellular Biochem. Suppl. 14C:253, Abstract 1008 (1990).
F. Rastinejad, Regulation of the Activity of a New Inhibitor of Angiogenesis by a Concern Suppressor Gene, Dissertation (Aug. 1988).

*Primary Examiner*—Jeffrey E. Russel
*Attorney, Agent, or Firm*—Tilton, Fallon, Lungmus & Chestnut

[57] ABSTRACT

A method of inhibiting angiogenesis and preparations for use therein are disclosed. The preparations comprise human thrombospondin in trimer or monomer form or a fragment thereof capable of inhibiting vascularization. The method and preparations are especially applicable to the treatment of solid tumors including skin cancers for controlling tumor neovascularization and thereby arresting tumor enlargement.

24 Claims, No Drawings

METHOD OF INHIBITING ANGIOGENESIS OF TUMORS

GRANT REFERENCES

The research leading to this invention was supported in part by NIH Grants RO1 CA27306 and RO1 HL39926. The U.S. Government has rights therein.

FIELD OF INVENTION

The field of this invention is angiogenesis of solid tumors. In particular, the invention is concerned with methods and therapeutic agents for inhibiting tumor neovascularization.

BACKGROUND OF INVENTION

As a normal cell develops into a solid tumor it undergoes a series of changes. At the genetic level, oncogenes are activated and multiple tumor suppressor genes are inactivated. At the physiological level, growth is enhanced, immunity evaded, and neovascularization induced. Neovascularization appears to be a prerequisite. Experimental solid tumors are unable to grow beyond a few millimeters in thickness without a blood supply. Most natural solid tumors elaborate angiogenic factors that attract the new vessels on which they depend. [For a discussion of angiogenic factors and the unsolved problem of how to inhibit tumor neovascularization, see Folkman and Klagsburn, *Science*, 235:442-447 (1987).] It has become increasingly evident that once a solid tumor has been established in the body every increase in tumor cell population must be preceded by an increase in new capillaries that converge upon the tumor. Consequently, there has been a continuing research effort directed toward the question of what prevents rampant capillary proliferation and what maintains the quiescent state of the capillary endothelial cells of normal tissues.

There has also been an active search for a therapeutic agent or agents which can cause capillary regression. Identification of such an agent has proven to be a very difficult problem. About the only demonstrable difference between tumor angiogenesis and other types of non-neoplastic angiogenesis is a greater intensity and persistence of the angiogenesis induced by tumors. It has become generally recognized that a therapeutic agent which can effectively inhibit tumor neovascularization should be of great value in limiting, or even completely stopping, the growth of tumors.

In one investigation of angiogenesis, Bouck, et al. carried out tests with a panel of cell hybrids derived from fusions between a chemically transformed hamster cell line and normal human fibroblasts [*Cancer Res.* 46:5101-5105 (1986)]. These researchers reported that anchorage independence of the cells (which in these cells is 100% correlated with tumor forming ability) is initially suppressed and that to remain repressed they must retain human chromosome 1. These researchers further found that the suppressed hybrids were unable to elicit an angiogenic response in a rat cornea assay. In contrast, those hybrids on which anchorage independence is expressed and which have lost human chromosome 1 were found to be potently angiogenic.

Dr. Noel Bouck, Dr. Peter J. Polverini and their associates in the Departments of Microbiology Immunology and Pathology of Northwestern University Medical School reported on further work with their hamster cell lines [Rastinejad, et al., *Proceedings*, 78th Ann. Meeting, Amer. Assoc. Cancer Res., Vol. 228:61, Abstract 241 (March, 1987)]. Exploration of the possibility that phenotypes of anchorage independence and angiogenesis depend on a common mediator, utilized the transforming growth factor (TGF-B). In testing for angiogenic activity, mixing experiments were performed to investigate the lack of angiogenic response to a mixture of normal baby hamster kidney (BHK) cells and a transformed cell line producing TGF-B. It was found that the normal BHK cells or their conditioned media inhibited angiogenesis when co-introduced with transformed cells into the cornea. It was concluded that secreted factors in the non-tumorogenic lines can negate the angiogenic response to TGF-B.

In 1988 these same investigators (Rastinejad, et al.) reported on the finding of an inhibitor of angiogenesis under control of a cancer suppressor gene [Proceedings, 79th Meeting, Amer. Assoc. Cancer Res., 29:45, Abstract 1809 (March, 1988)]. It had been reported that in a normal baby hamster kidney (BHK) cell line, inactivation of a suppressor gene by carbinogen treatment permitted the expression of anchorage independence and tumorgenicity [Bouck and Head, *In Vitro Cell and Devel. Biol.* 21:463 (1985)]. Significantly, this loss of suppressor gene function coincided with loss of the ability to elaborate a factor that inhibits neovascularization in the right rat cornea, but anchorage dependent revertants were unable to suppress transformation infusions and failed to produce the inhibitor. Using the ability of this unknown factor to inhibit bovine endothelial cell migration in a modified Boyden chamber, the factor was purified to apparent homogeneity. These results suggested that one function of the cancer suppressor gene present in the normal BHK cells is to mediate the release of an inhibitor of the antiogenesis that is vital to progressive growth of tumors.

SUMMARY OF INVENTION

This invention is based in part on the unexpected discovery that the BHK cell angiogenesis inhibitor of unknown structure corresponds to a 140 kD fragment of human thrombospondin [Good, et al., UCLA Symposia, Jan. 21-Feb. 11, 1989, *J. Cellular Biochem., Suppl.* 13B:30, Abstract D215]. A strong cross-reaction was observed with the 140 kD BHK inhibitor using a monoclonal antibody to thrombospondin, and polyclonal antibodies to the BHK inhibitor recognized thrombospondin purified from human platelets. Moreover, sequencing of an amino-terminal 20-amino acid sequence of the BHK inhibitor showed that at least 16 of 20 residues were identical to a sequence in human platelet thrombospondin beginning at residue 294. Further, the total amino acid composition of the BHK inhibitor was exceedingly similar to that predicted from the cDNA sequence from human thrombospondin from residue 294 to its carboxyl terminus. Also, in a corneal assay, human thrombospondin and the BHK inhibitor were both able to block the basic-fibroblast growth factor (bFGF)induced neovascularization at the same concentration. [See Bouck, et al., *Current Commun. Molecular Biol.* in "Recessive Oncogenes and Tumor Suppression", Cavenee, et al., eds., pages 179-183 (Cold Spring Harbor Laboratory Press, 1989); and Rastinejad, et al., *Cell*, 56:345-355 (Feb. 10, 1989)].

The present invention is directed to the treatment of human patients having growing solid tumors with associated neovascularization and to the treatment of other diseases where neovascularization is a contributory factor to progression of the disease. A preferred method of retarding the tumor growth of this invention comprises administering to the site of the patient's tumor a neovascularization inhibitor consisting of human thrombospondin or fragments thereof capable of inhibiting vascularization. In carrying out the treatment the inhibitor should be present in the environment of the treated tumor in an amount effective for retarding enlargement of the tumor. With respect to other diseases requiring control of neovascularization, the amount of the inhibitor used should be effective for inhibiting the neovascularization at the site where it is occurring.

DETAILED DESCRIPTION

In developing the present invention, the BHK angiogenesis inhibitor was purified as described in Rastinejad, et al. (1989) cited above. This inhibitor was found to be a glycoprotein of about 140 kD molecular weight, which glycoprotein corresponded closely with the amino acid structure of the human thrombospondin monomer fragment from residue 294 to its carboxyl terminus. The BHK inhibitor was compared with human thrombospondin in its natural trimer form using a rat corneal assay as described in Bouck, et al. (1986), cited above. The test materials were mixed 1:1 with Hydron (poly-2-hydroxy-ethyl-methacrylate). Small pellets containing a defined amount of the test material were implanted into the cornea of the rat eye either with or without 50 ng of the basic-fibroblast growth factor (bFGF). Positive responses were recorded when sustained growth of new blood vessels from the limbus toward the implant was observed by 7 days. Results are summarized below in Table A.

TABLE A

| Inhibition of Corneal Neovascularization By Hamster Cell gp140 Inhibitor and Thrombospondin | | |
|---|---|---|
| | Positive Corneas/Total | |
| Test Material | +bFGF | −bFGF |
| Buffer | 4/4 | 0/3 |
| gp140 inhibitor | | |
| 0.025 ug | 3/3 | 0/2 |
| 0.125 ug | 0/3 | 0/2 |
| 0.625 ug | 1/3 | 0/3 |
| thrombospondin | | |
| 0.025 ug | 3/3 | 0/2 |
| 0.125 ug | 0/4 | 0/2 |
| 0.625 ug | 0/3 | 0/2 |

As shown by the foregoing data, human thrombospondin has comparable inhibitor activity to the gp140 BHK inhibitor.

Human thrombospondin (HTSP) is a glycoprotein found in the alpha granules of platelets. It is secreted from platelets upon activation by various agonists. HTSP has been extensively studied in trimer, monomer, and fragmented forms. [See, for example, Santoro and Frazier, *Methods in Enzymology*, 144:438–446 (1987); Majack and Bornstein, *Cell Membranes Methods-Reviews*, 3:55–77 (1987); and Haverstick, et al., *Biochemistry*, 23:5597–5603 (1984).] The cited Majack and Bornstein on page 59, FIG. 2, diagrams the relation of the natural trimer to enzymatic degradation fragments. The human thrombospondin gene has been cloned and the thrombospondin monomer has been sequenced. [See Lawler and Hynes, *J. Cell Biol.*, 103:1635–1648 (1986); Donoviel, *J. Biolog. Chem.*, 263:18590–18593 (1988); and Hennessy, et al., *J. Cell Biol.*, 108:729–736 (1989).]

Thrombospondin in its natural trimer form is a 420 kD glycoprotein. The individual monomers, which are disulfide-linked to form the trimeric structure, have a linear series of discrete functional domains that contain multiple binding sites. These domains include a heparin binding domain associated with an amino terminal end portion, a plasminogen binding domain in the central region, and a platelet binding domain associated with a carboxyl terminal end portion. Again, reference is made to Majack and Bornstein, cited above, page 59, FIG. 2.

As described by Santoro and Frazier (1987), Majack and Bornstein (1987), and Haverstick, et al. (1984), all cited above, fragments of thrombospondin can be readily prepared by enzymatic digestions. Enzymes such as chymotrypsin, thrombin, trypsin, elastase, and thermolysin cleave 25 to 35 kD segments from the amino end of the monomers. The remaining 140 kD fragments remain united in trimer form. When chymotrypsin or thermolysin is employed for the enzymolysis, the monomers are also reduced to 120 kD fragments, which not only have their amino ends trimmed as described but also have an 18–25 kD segment trimmed from their carboxyl ends. The 25–35 kD fragment contains a heparin binding site while the 18–25 kD fragment contains a platelet binding site. A mixture of both the 120 kD and the 140 kD fragments can be produced in the same procedure.

The 140 kD and 120 kD fragments are usually obtained in trimer form, and can be resolved into monomer form by incubation with dithiothreitol. When the trimer of the 140 kD fragment or the trimer of the 120 kD fragment is enzymatically treated with chymotrypsin in the presence of EDTA (ethylenediaminetetraacetic acid), two further fragments are obtained, a 70 kD fragment extending from the amino end of the 120 kD fragment and a 50 kD fragment extending from the carboxyl end of the 120 kD fragment. The 70 kD and the 50 kD fragments are in monomer form. The 50 kD fragment contains the binding region for fibrinogen. The 70 kD fragment contains the region that functions as an angiogenesis inhibitor, and is usable for the purposes of the present invention. This being true, it is to be expected that further fragmentation of the 70 kD fragment should be possible.

Methods exist for confirming whether or not the inhibitor activity against neovascularization is retained, thus making it easy to confirm usefulness for the purposes of this invention. Available methods include the rat corneal assay. Selected fragments can be produced by genetic engineering methods as recombinant fragments, since the gene for HTSP has been isolated and cloned (citations given above). Other variations are also expected to be feasible. These include deglycosylated forms of HTSP trimer, monomer, or fragments, which can be prepared by known procedures for deglycosylating glycoproteins. [See Edge, et al., *Analyt. Biochem.*, 118:131–137 (1981) for a deglycosylation procedure using trifluoromethanesulfonic acid.] Alternatively, the HTSP gene for the monomer or gene segments for fragments thereof can be expressed in cells which do not result in glycosylation of the monomer. Although it may be preferred to use glycosylated forms of the HTSP inhibitors of this invention, this is not believed to be essential. Furthermore, for production of inhibitors by biochemical or by genetic engineering procedures, deglycosylated forms may be less expensive than glycosylated forms.

Since thrombospondin is a multiple domain glycoprotein having other bodily functions, it is preferred to administer the inhibitors of this invention by extravascular procedures. For example, HTSP is known to cause platelet aggregation, and therefore in its natural form it would be inadvisable to administer HTSP by a parenteral route. However, by trimming HTSP fragments as described above, or by using a selected sequence of the HTSP gene to produce trimmed forms, inhibitors can be produced which contain primarily the active region which inhibits angiogenesis. It may therefore be safe to administer such modified fragment forms by parenteral routes.

Effective extravascular routes are available. For internal tumors, the inhibitor can be directly implanted by known techniques. For example, it can be combined with slow release polymers such as poly-2-hydroxyethylmethacrylate or methylenevinylacetate copolymer. When combined with such retardants, the inhibitor can be prepared in the form of pellets of known inhibitor content, and selected quantities of the pellets can be directly implanted in the tumor. For skin tumors, which are also classified as solid tumors, the inhibitor can be combined with a topical ointment and applied directly to the surface of the tumor. Procedures for preparing such administration vehicles whether for pellet implantation or for direct surface application are further described in the following examples. Other procedures which may be useful include the preparation of the inhibitor in aerosol form for application to lung tumors, using standard devices employed by respiratory therapists to deliver aerosols.

In general, it is believed that the inhibitors of this invention will be of greatest value for arresting the growth of rapidly growing tumors like melanomas. However, all solid tumors are dependent for growth on the generation of new capillary vessels, and the method of this invention is believed to be generally applicable to internal solid tumors and to all forms of cancer growing in the skin. When a solid tumor is surgically removed, an implant may be placed at the site of the removed tumor, thereby inhibiting the angiogenesis of any re-forming tumor at the same site.

The required dose for lessening enlargement of a tumor will vary with the size and location of the tumor. Amounts may rang from 1 microgram (ug) to 1 milligram (mg). It is believed that preferred amounts will usually range from 100 ug to 800 ug quantities per dose. In general, an amount will be applied to the site of the tumor sufficient to retard growth of the tumor. The amount required for this purpose can be monitored by standard procedures. Where the tumor is still growing despite the application of the inhibitor, additional quantities will be administered. Preferably, a sufficient dose is utilized to substantially stop the increase of tumor size, or in some cases to decrease the size of the tumor. Such a result can be observed by a number of methods, depending on the location and type of tumor involved. These methods include: visual observation of surface tumors, palpitation, radiological measurement (viz., X-rays for lung tumors, mammograms for breast tumors, etc.), use of ultrasound with computer assisted tomographic scanners (CAT scans), magnetic resonance imaging, radionucleotide scanning, and other standard clinical techniques used to monitor particular tumor types.

In addition to solid tumors, the inhibitors of this invention may be used as therapeutic agents for other diseases involving angiogenic dysfunction. These diseases include diabetic retinopathy, retrolental fibroplasia, neovascular glaucoma, psoriasis, angiofibromas, immune and non-immune inflammation (including rheumatoid arthritis), capillary proliferation within atherosclerotic plaques, hemangiomas, Kaposi's Sarcoma, endometriosis, and unwanted scar formation in wound healing. The amount to be used should be sufficient to partially or completely prevent the angiogenesis at the site where it is occurring.

The preparation of inhibitors useful in the method of the present invention and their modes of administration are further illustrated by the following examples.

EXAMPLE 1

Preparation of Pure Human Thrombospondin (HTSP) From Whole Blood

Whole human blood, preferably freshly collected in ACD (8 g/L citric acid, 22 g/L trisodium citrate, 24.5 g/L glucose, pH, 4.5), 9 parts blood to 1 part ACD, is centrifuged at $180 \times g$ for 15 minutes at room temperature. The platelet rich plasmia (PRP) is transferred to a new tube and 1/5 volume of ACD is added. The platelets are pelleted by centrifugation at $1100 \times g$ for 10 minutes at room temperature, and then resuspended in buffer containing 0.15 M NaCl, 4.3 mM $K_2HPO_4$, 4.3 mM $Na_2HPO_4$, 24 mM $NaH_2PO_4$, 5 mM glucose, pH 6.5. The platelets are washed twice in the above buffer, and then resuspended in 8 ml of TCS buffer (0.15 M NaCl, 0.02 M Tris, pH 7.6, 1 mM $CaCl_2$) containing 5 mM glucose per unit of platelets. The washed platelets ar activated by addition of 0.5 U/mL of human thrombin (Sigma) and incubated at 37° C. for 1–2 minutes, until large aggregates are formed. The reaction is stopped by addition of 4 U/mL hirudin and 2 mM phenylmethylsulfonyl fluoride (PMSF) (Sigma). The material is centrifuged at $1000 \times g$. Fibronectin is removed from the supernatent by chromatography on gelatin-sepharose (Pharmacia) equilibrated with TCS buffer at 4° C. The flow through material is collected and loaded onto a heparin-Sepharose column (Pharmacia) equilibrated with TCS buffer, and washed with 0.25 M NaCl and the thrombospondin eluted by increasing the NaCl concentration to 0.6 M. To remove low molecular weight contaminants the eluent is loaded onto a Bio-Gel A 0.5 m column (Bio Rad Laboratories) equilibrated with TCS buffer. The thrombospondin elutes in the void volume and is stored at −70° C. in TCS buffer containing 20% w/v sucrose. [See Santoro and Frazier, *Methods in Enzymology*, 144:438–446 (1987) for analogous method.]

EXAMPLE 2

Reduction of Pure Human Thrombospondin (HTSP) to Its Monomeric Form

Pure thrombospondin trimer is incubated in 25 mM dithiothreitol (DTT) (or higher DTT concentration if found to be necessary) at 37° C. for 1 hour. The DTT is then removed from the thrombospondin preparation by dialysis against two changes of a $1000 \times$ excess of TCS buffer at 4° C. A portion of the preparation is checked for complete reduction of the 450 kD trimeric form to the 180 kD monomeric form on a 6% non-reducing polyacrylamide gel.

EXAMPLE 3

Derivation of the 140 kD and 120 kD Fragments of Human Thrombospondin

To produce a 140 kD fragment of thrombospondin from the 180 kD, the calcium-replete monomer is treated with 4 U/mL thrombin for 1 hour at 37° C. Alternatively, the calcium-replete thrombospondin monomer can be treated with L-1-tosylamido-2-phenylethylchloromethyl ketone-treated trypsin (TPCK-treated trypsin) at an enzyme to substrate ratio of 1:20 for 5 minutes at 22° C. The reactions are stopped using 1 mM diiodopropyl fluorophosphate (DFP) for thrombin. The fragments can be further purified by gel chromatography over a heparin-Sepharose column equilibrated with TCS buffer at 4° C. The 140 kD fragments, lacking the N-terminal heparin binding domain, will elute in the flow through, whereas undigested whole thrombospondin will be retained. Alternatively ion exchange chromatography can be used to separate the two species.

The 120 kD fragment lacking both the N-terminal 30 kD and the C-terminal 25 kD domains is produced by treatment of thrombospondin with 4 U/mL thrombin for 120 minutes at 22° C. The reaction is stopped as above. [See Lawler, et al., *J. Cell. Biol.* 260:3762 (1987) for analogous method.] For each of the above reactions, the desired fragments can be further purified by ultrafiltration through a YM membrane (Amicon) or by gel filtration.

EXAMPLE 4

Derivation of Thrombospondin 70 kD Subunits

To produce 70-kD monomeric fragments of thrombospondin, calcium replete thrombospondin is dialyzed into TBS (0.02 M Tris, pH 7.6, 0.15 M NaCl) containing either 5 mM EDTA or 10 mM $Mg^{++}$ [Dixit, et al., *J. Biol. Chem.* 261:1962 (1986)] followed by digestion of this calcium-depleted thrombospondin with 0.5% chromotypsin (Sigma) or 15 minutes at 25° C. The reaction may be terminated as described in Example 3 or by other suitable reagent. The digest is applied to a Sephadex G-100 column equilibrated with TBS and the 70 kD trimer eluted from the column [Galvin, et al., *J. Cell Biol.* 104:1413 (1987)].

EXAMPLE 5

Reduction of the Trimeric Fragments of Thrombospondin to the Monomeric 140 kD, and the 120 kD and 70 kD Fragments The 140 kD, 120 kD, and 70 kD fragments if in trimer forms can be reduced to their monomeric forms using the procedure of Example 2.

EXAMPLE 6

Deglycosylation of Intact Thrombospondin and Its Trimer or Monomer Fragments N-linked oligosaccharides can be removed by the following protocol. A 20 ug sample (2 ug/uL) of whole thrombospondin or one of its fragments, isolated as described above in 0.5% SDS, is incubated for 1 hour at 37° C. Following this incubation, 10.8 ul of 0.55 M sodium phosphate, pH 8.6, is added along with 3 uL of 100 mM 1,10-phenanthroline hydrate in methanol, and 5 uL of 7.5% NP-40. N-glycanase (250 U/mL, Genzyme) is added to a final concentration of 2.5 u/mL. The sample is incubated for 2 hours at 37° C. Following this incubation, the sample is checked for loss of carbohydrate moiety by analysis on 6% SDS-polyacrylamide gels [Laemmeli, *Nature*, 227:680 (1970)]. The unglycosylated sample is applied to a Superose gel filtration column (Pharmacia) equilibrated with PBS at 4° C. and proteins are eluted in the same buffer. The major protein peak at the molecular weight corresponding to approximately 6% less than that size is expected from the glycosylated peptide taken, and dialyzed against TCS using a centricon-30 microconcentrator. An alternate method that can be used in conjunction with the above method to remove O-linked carbohydrates is described in Edge, et al., *Analyt. Biochem.*, 118:131–137 (1981).

EXAMPLE 7

Procedure for Preparing Injectable or Implantable Slow Release Pellets

Microgram quantities of HTSP (monomer or trimer) prepared as described in Examples 1 and 2, or an active TSP fragment prepared as described in Examples 3 to 6 are incorporated into one of several slow-release noninflammatory polymers. The two most often used are poly-2-hydroxylethyl-methacrylate (Hydron$^R$ Lot No. 110, Interferon Sciences, Inc., New Brunswick, N.J.) and ethylene-vinyl acetate copolymer (EVA, Aldrich Chemical, Milwaukee, Wid.). Both materials work with equal effectiveness. [See Langer and Folkman, *Nature*, 263:797–800 (1976), for descriptions of preparations and use of these retardants.]

For example, sterile casting solutions of Hydron$^R$ are prepared by dissolving the Hydron powder in absolute ethanol (12% w/v) at 37° C. with continuous stirring for 24 hrs. An equal volume of Hydron and the active agent (e.g., HTSP) (50%) are combined and 10 ul of solution are pipetted onto the surface of a sterile 3.2 mm diameter, 1.2 cm long Teflon$^R$ (DuPont Corp.) rods glued to the surface of a petri dish. After drying for 1-2 hrs the approximately 2 mm diameter disks can then be stored at 4° C. or can be implanted immediately.

Alternatively EVA pellets are prepared by dissolving them, 40% by weight in methylene chloride at 37° C. The active agent (e.g., HTSP) is then added to the EVA solution and small (10 ul) quantities are pipetted into glass molds and air dried under vacuum. Dried pellets are washed extensively, 10-15 changes, in methanol to remove any free methylene chloride. The pellets are then ready for administration.

EXAMPLE 8

Administration of Slow Release Pellets

Pellets prepared as described in Example 7 can be implanted into solid tumors with the use of a wide bore (16 gauge) trochar for the precise positioning of the pellets. Under anesthesia, pellets containing 1 ug to 1 mg quantities of TSP monomer, or trimer, or active fragments are loaded into the barrel of the trochar. Several pellets can be positioned at a single location or at multiple sites within the tumor. To study the potency of the inhibitory response, angiographic studies are performed to assess whether there has been any retardation or regression of tumor vessels. Once the tumor has stopped growing or has undergone a marked reduction in size, it can be removed. Alternatively implantation can be repeated, particularly with large tumors where prolonged exposure to the inhibitor is necessary to reduce the tumor size.

EXAMPLE 9

Treatment of Skin Cancers

The inhibitors described herein can also be formulated into ointments or suspensions in combination with purified collagen in order to produce semisolid or suspension vehicles. Conventional oleaginous formulations containing the inhibitor can be used as salves. Such formulations will release the inhibitor on a sustained basis at the skin cancer site.

Purified human skin collagen obtained from commercially available sources can be used in the ointments. The inhibitor can be incorporated into the collagen solution where under alkaline conditions the collagen inhibitor solution will gel. Thin films can be prepared by dispensing the liquid collagen inhibitor atop glass plates. The thin sheets can then be placed atop a skin surface growing cancer and covered by a semipermeable membrane to allow for air exchange. Alternatively, the inhibitor can be incorporated in one of several petroleum jelly-based materials along with dimethyl sulfoxide to increase absorption of the inhibitor into the skin tumor, and applied as a salve where it could be applied several times a day to the surface cancer. It may be necessary to scarify the surface of the tumor to enhance penetration of the inhibitor into the neoplasm.

The types of surface cancers where this might be useful include but are not limited to basal cell carcinoma, squamous cell carcinoma and melanoma. The frequency of topical application can be judged empirically by periodically checking for reduction in tumor size.

EXAMPLE 10

Test Procedures to Confirm the Inhibitor Effect of TSP Fragments

Human thrombospondin fragments prepared from human platelets or prepared from segments of the human thrombospondin gene can be tested to confirm inhibitory activity against angiogenesis by a number of established procedures. All of the following procedures are believed to be usable for this purpose. To confirm the inhibitory effect determination, two or more of the following assays can be used.

A. Assay of TSP Fragments for Inhibitory Activity in the Rat Cornea

The surgical procedure used to form a corneal pocket is essentially identical to that first described by Gimbrone, et al., *J. Natl. Cancer Inst.* 52:413-427 (1974), for rabbit cornea. Imbred F344 rats are available for routine use, but any rate strain is suitable. Male or female rats weighing 150-200 gm are anesthetized with sodium pentobarbital (29 mg/kg body wt). The eyes are gently proptosed and secured in place by clamping the upper eyelid with a nontraumatic hemostat Using a No. 11 Bar Parker blade a 1.5 mm incision is made approximately 1 mm from the center of the cornea into the stroma but not through it. Depending on experience this procedure can be done with or without the use of a dissecting scope. A curved iris spatula (No. 10093-13, Fine Science Tools, Inc., Belmont, Calif.) approximately 1.5 mm in width and 5 mm in length is then inserted under the lip of the incision and gently blunt-dissected through the stroma toward the outer canthus of the eye. Slight finger pressure against the globe of the eye helps steady it during dissection. The spatula is premarked so that the shaft does not penetrate laterally into the stroma more than 2.5 mm. Once the corneal pocket is made the spatula is removed and the distance between the limbus and base of the pocket is measured to make sure it is no closer than 1 mm. The pocket base is typically between 1-1.5 mm from the limbus. (Extending the pocket depth any closer than this often results in a false positive response. Also if the depth of incision is too close to the inner surface of the cornea nonspecific inflammation invariably occurs.)

The first 24-48 hours after implantation are critical. If nonspecific inflammation is to occur it will manifest during this time. In such cases corneal clouding and the presence of a yellowish exudate signals inflammation. As long as asepsis is maintained and trauma during surgery is minimized, nonspecific inflammation will rarely be a problem. Even in the most carefully executed procedure some transient corneal edema will occur. However, this usually resolves within 24 hrs. Just before implanting Hydron or EVA pellets containing the pure TSP fragments being tested, the pellets are rehydrated with a drop of sterile lactated ringers solution. Pellets are then positioned down to the base of the pocket which then seals spontaneously. No more than half of the pocket should be occupied with implant material. More than this the resultant transient edema will cause spontaneous expulsion of the implant. Corneas are examined daily or on alternate days with the aid of a stereomicroscope to monitor responses.

Scoring of Vascular Responses: The corneal bioassay is sometimes regarded as a qualitative assay, but a numerical quantitative measure has been devised for use with this model system. Responses are usually scored on the day animals are killed, 5-7 days after implantation. Positive responses are recorded when sustained ingrowth of capillary loops or sprouts is detected. Negative scores are assigned to responses where either no growth is detected or when an occasional sprout or hairpin loop is detected without evidence of sustained growth is observed. Occasionally (10% of the time) responses are encountered that are neither equivocally positive nor negative with samples which are normally positive or inhibitory. In these instances, the responses can be graded. Several factors account for this, i.e., slight differences in the position of implants within the cornea, variations in the quantity and quantity of material being tested. (This technique inherently involves a degree of variability, but this can be kept at a minimum).

Preparation of colloidal carbon perfused whole mounts: Permanent records of vascular response are made following perfusion with india ink. Commercially available waterproof india ink is usable. Perfusion is accomplished with a simple pressure vessel capable of maintaining a pressure of 120 mm/Hg. Perfusion via the abdominal aorta is carried out, introducing 100-200 ml warm (37° C.) lactated ringers solution per 150 gm rat. Once the animal's snout has completely blanched, approximately 20-25 ml of ink is injected until the head and thoracic organs have completely blackened. Eyes are then carefully enucleated and placed in half-strength Karnovsky's fixative or neutral buffered formalin for 24 hours. The next day corneas are dissected free from the surrounding globe and underlying iris, are bisected and loosely mounted between two glass slides where they are gently flattened. Corneas are photographed with a dissecting microscope equipped with a camera. If desired, the response can be quantitated. For example, vessel length can be measured directly using 4×5 transilluminated photographic negatives at a magnification of 10×. Three radially oriented measurements are taken using a vernier caliper; two of these measurements include vessels present at the periphery of the radius and the third includes the largest vessels along the center of the radius. The three measurements are averaged to provide a single length of measure for each response. Differences between groups are compared using a students t-test.

B. Assays for Angiogenic Activity In Vitro

Endothelial Cell Chemotaxis: Endothelial cell migration can be assayed using a 48-well modified Boyden chamber (Nucleopore Corp) equipped with Nucleopore membranes (5 u pore size) that have been soaked overnight in 3% acetic acid, incubated for 2 hours in 0.1 mg/ml gelatin, rinsed in sterile water, dried under sterile air, and stored for up to 1 month. BCE cells usually not older than passage 10 are preferred. (Older cultures may show greater variability in responsiveness to chemotactic stimuli. Also, differences in the responsiveness of endothelial cells to chemotactic stimuli vary from isolate to isolate so comparisons should be made within each experiment.)

Chambers are set up using $5 \times 10^5$ cells suspended in 1.5 ml of DME media supplemented with 0.1% FBS. The bottom wells are filled with 25 ul of the cell suspension and covered with the gelatin-coated membrane. The chamber is assembled and then inverted and incubated for 2 hrs to permit adherence of BCE to the membrane surface. This modification of the standard assay is important since the inhibitory activity may interfere with adhesion of BCE to the membrane surface. The chamber is then turned upright, 50 ul of the TSP fragment (about 1-2 ug) along with 50 ng of FGF is dispensed into the top wells, and the chamber is incubated for an additional 2-3 hrs. The membrane bound cells are carefully washed with buffered saline, stained with DiffQuick stain (American Scientific Products), and membranes are mounted with Permount$^R$ (Fisher Scientific) or taped to the slide with the surface to which the cells have migrated up. The number of cells which have migrated per 10 high powered (×100) fields are counted. By focusing through the membrane it is possible to distinguish the surface of the membrane to which cells have migated

C. Chicken Chorioallantoic Membrane (CAM) Assay

Fertile eggs are incubated in a stationary position for 3 days at 37° C. and 70-80% relative humidity. During this time, the embryo rises to the upper surface of the egg contents. At the beginning of the 4th day, the eggs are cracked without inversion and carefully deposited into sterile plastic petri dishes such that the embryo remains on the upper surface. The shell-free eggs are incubated for an additional 72 hours at 37° C., under an atmosphere containing 2.5-3.5% $CO_2$, after which the growing embryos develop a recognizable CAM. Discs, made by mixing test samples with 1% (w/v) methylcellulose, are dried and placed on the CAM between major veins and approximately 0.5 cm from the embryo. Following another 48 hour incubation at 37° C. (1.5-3.5% $CO_2$), the samples are scored for their ability to inhibit angiogenesis. Inhibition appears as an avascular zone surrounding the implant and can often include elbows formed by veins avoiding the disc and a reduced number of capillaries in the region of the implant.

We claim:

1. A method of inhibiting angiogenesis in a human patient, comprising administering to the patient a vascularization inhibitor comprising substantially pure human thrombospondin in trimer or monomer form, or a substantially pure fragment thereof capable of inhibiting vascularization.

2. The method of claim 1 in which said thrombospondin is in trimer glycosylated form.

3. The method of claim 1 in which said thrombospondin is in monomer glycosylated form.

4. The method of claim 1 in which said inhibitor corresponds essentially with a glycosylated trimer composed of the approximately 140 kilodalton (kD) fragments obtainable by enzymatic digestion of natural human thrombospondin, said fragments not containing a heparin binding domain associated with the amino end portion of the natural thrombospondin monomer.

5. The method of claim 1 in which said inhibitor corresponds essentially with a glycosylated trimer composed of the approximately 120 kilodalton (kD) fragments obtainable by enzymatic digestion of human thrombospondin, said fragments not containing either the heparin binding domain associated with the amino end portion of the thrombospondin monomer or the platelet binding domain associated with the carboxyl end portion of the thrombospondin monomer.

6. The method of claim 1 in which said inhibitor is a monomer corresponding essentially with the 140 kilodalton (kD) fragments obtainable by enzymatic digestion of human thrombospondin, said fragments not containing a heparin binding domain associated with the amino end portion of the thrombospondin monomer.

7. The method of claim 1 in which said inhibitor corresponds essentially with a glycosylated monomer composed of the approximately 120 kilodalton (kD) fragments obtainable by enzymatic digestion of human thrombospondin, said fragments not containing either the heparin binding domain associated with the amino end portion of the thrombospondin monomer or the platelet binding domain associated with the carboxyl end portion of the thrombospondin monomer.

8. The method of claim 1 in which said inhibitor corresponds with the approximately 70 kD monomer fragments obtainable by enzymatic digestion of the 120 kD monomer fragments, of human thrombospondin, said 70 kD fragments not containing a fibrogen binding domain associated with the carboxyl end portion of said 120 kD monomer.

9. The method of claim 1 in which the patient is being treated for an internal tumor, and said inhibitor before administration is admixed with a slow release agent and thereafter a portion of the mixture is implanted in the tumor.

10. The method of claim 1 in which the tumor being treated is a skin cancer and said inhibitor before administration is admixed with a topical vehicle and thereafter applied to the surface of the skin cancer.

11. The method of claim 1 in which said inhibitor corresponds with a fragment of the human thrombospondin trimer which contains a region capable of inhibiting angiogenesis as determined by the rat corneal assay, said fragment being in trimer or monomer form, and said trimer and monomer forms being either glycosylated or non-glycosylated.

12. The method of claim 11 in which said fragment is in a glycosylated form.

13. In the treatment of human patients having growing solid tumors with associated neovascularization, the method of retarding tumors growth comprising administering to the site of the patient's tumor a vascularization inhibitor comprising substantially pure human thrombospondin in trimer or monomer form, or substantially pure fragments thereof capable of inhibiting vascularization, said inhibitor being applied to the tumor in an amount effective for retarding its enlargement.

14. The method of claim 13 in which said inhibitor corresponds with a fragment of the human thrombospondin trimer which contains a region capable of inhibiting angiogenesis as determined by the rat corneal assay, said fragment being in trimer or monomer form, and said trimer and monomer forms being either glycosylated or non-glycosylated.

15. A therapeutic product for controlling angiogenesis, comprising implantable pellets composed essentially of a slow release agent in admixture with a vascularization inhibitor comprising substantially pure human thrombospondin in trimer or monomer form, or substantially pure fragmented thereof capable of inhibiting vascularization.

16. A therapeutic product for controlling angiogenesis, comprising a topical vehicle in admixture with a vascularization inhibitor comprising substantially pure human thrombospondin in trimer or monomer form, or substantially pure fragments thereof capable of inhibiting vascularization.

17. The therapeutic preparations of claims 15 or 16 in which thrombospondin is in its trimer glycosylated form.

18. The therapeutic preparations of claims 15 or 16 in which said thrombospondin is in monomer glycosylated form.

19. The therapeutic preparations of claims 15 or 16 in which said inhibitor corresponds essentially with a glycosylated trimer composed of the approximately 140 kilodalton (kD) fragments obtainable by enzymatic digestion of human thrombospondin, said fragments not containing a heparin binding domain associated with the amino end portion of the natural thrombospondin monomer.

20. The therapeutic preparations of claims 15 or 16 in which said inhibitor corresponds essentially with a glycosylated trimer composed of the approximately 120 kilodalton (kD) fragments obtainable by enzymatic digestion of human thrombospondin, said fragments not containing either the heparin binding domain associated with the amino end portion of the thrombospondin monomer or the platelet binding domain associated with the carboxyl end portion of the thrombospondin monomer.

21. The therapeutic preparations of claims 15 or 16 in which said inhibitor is a monomer corresponding essentially with the 140 kilodalton (kD) fragments obtainable by enzymatic digestion of human thrombospondin, said fragments not containing a heparin binding domain associated with the amino end portion of the thrombospondin monomer.

22. The therapeutic preparations of claims 15 or 16 in which said inhibitor corresponds essentially with a glycosylated trimer composed of the approximately 120 kilodalton (kD) fragments obtainable by enzymatic digestion of human thrombospondin, said fragments not containing either the heparin binding domain associated with the amino end portion of the thrombospondin monomer or the platelet binding domain associated with the carboxyl end portion of the thrombospondin monomer.

23. The therapeutic preparations of claims 15 or 16 in which said inhibitor corresponds with the approximately 70 kD monomer fragments obtainable by enzymatic digestion of the 120 kD monomer fragments of human thrombospondin, said 70 kD fragments not containing a fibrogen binding domain associated with the carboxyl end portion of the 120 kD monomer.

24. The therapeutic preparations of claims 15 or 16 in which said inhibitor corresponds with a fragment of the human thrombospondin trimer which contains a region capable of inhibiting angiogenesis as determined by the rat corneal assay, said fragment being in trimer or monomer form, and said trimer and monomer forms being either glycosylated or non-glycosylated.

* * * * *

UNITED STATES PATENT AND TRADEMARK OFFICE
CERTIFICATE OF CORRECTION

PATENT NO. : 5,192,744
DATED : March 9, 1993
INVENTOR(S) : Bouck et al.

It is certified that error appears in the above-identified patent and that said Letters Patent is hereby corrected as shown below:

Column 8, line 28, delete "Wid." and add "WI"

Signed and Sealed this

Twenty-third Day of November, 1993

Attest:

BRUCE LEHMAN

*Attesting Officer*   *Commissioner of Patents and Trademarks*